United States Patent [19]
Stoev et al.

[11] Patent Number: 5,427,664
[45] Date of Patent: Jun. 27, 1995

[54] FREE SOLUTION ELECTROPHORESIS-MEMBRANE FILTERS TRAPPING ASSAY APPARATUS AND METHOD

[76] Inventors: Stoyan V. Stoev, 4046 N. Mozart, Chicago, Ill. 60618; Cvetan Strshenovsky, 5133 W. 22nd Pl., Cicero, Ill. 60650

[21] Appl. No.: 95,960

[22] Filed: Jul. 22, 1993

[51] Int. Cl.$^6$ .................. G01N 27/26; G01N 27/447
[52] U.S. Cl. ..................... 204/182.3; 204/301; 204/299 R; 204/182.8; 204/180.1
[58] Field of Search ............. 204/299 R, 182.8, 180.1, 204/301, 182.3, 182.6

[56] References Cited

U.S. PATENT DOCUMENTS

| | | | |
|---|---|---|---|
| 3,374,166 | 3/1968 | Raymond | 204/299 R |
| 3,533,933 | 10/1970 | Strauch | 204/182.8 |
| 4,479,861 | 10/1984 | Hediger | 204/299 R X |
| 5,078,853 | 1/1992 | Manning et al. | 204/299 R |

OTHER PUBLICATIONS

P. Greg Waterbury and Michael J. Lane "Generation of lambra phage concatemers for use as pulsed field electrophoresis size markers" Nucleic Acids Research, vol. 15 No. 9 (1987) (no month available) 3930.

Blazek et al.; "Evidence from Nondenaturing Filter Elution that Induction of Double-Strand Breaks in the DNA of Chinese Hamster V79 Cells by γ Radiation Is Proportional to the Square of Dose"; *Radiation Research* 119, 466–477 (1989) no month available.

D. Blöcher; "DNA double strand breaks in Ehrlich ascites tumour cells at low doses of X-rays.I. Determination of induced breaks by centrifugation at reduced speed"; *International Journal of Radiation Biology*, vol. 42, No. 3, 317–328 (1982) no month available.

Bradley et al.; "X-ray induced DNA double strand break production and repair in mammalian cells as measured by neutral filter elution"; *Nucleic Acids Research*, vol. 7, No. 3, 793–804 (1979) no month available.

Viovy et al.; "Irreversible trapping of DNA during cross-field gel electrophoresis"; *Electrophoresis*, 13, 1–6, (1992) no month available.

Edited by K. E. Davies; "Genome Analysis-a Practice Approach"; 41–63 (1988) no month available.

Stamato et al.; "Asymmetric Field Inversion Gel Electrophoresis: A New Method for Detecting DNA Double-Strand Breaks in Mammalian Cells"; *Radiation Research*, 121, 196–205 (1990) no month available.

(List continued on next page.)

*Primary Examiner*—John Niebling
*Assistant Examiner*—John S. Starsiak, Jr.
*Attorney, Agent, or Firm*—Wood, Phillips, VanSanten, Clark & Mortimer

[57] ABSTRACT

A free solution electrophones-membrane filter trapping assay apparatus includes a container and at least one porous membrane. The porous membrane and container define a chamber capable of holding run solution. A specimen containing particles to be classified is juxtaposed with the run solution. A voltage is placed across the specimen, run solution and membrane to cause particles to be released from the specimen. Particles enter the run solution and readily pass therethrough. Particles that are smaller in size than the pores of the membrane pass through the membrane while particles having a larger particle size do not. A method of classifying particles includes the steps of providing a sample of particles and a porous membrane, positioning a run solution between the sample and the membrane and applying an initial voltage across the sample, run solution and membrane.

15 Claims, 2 Drawing Sheets

OTHER PUBLICATIONS

Blöcher et al.; "CHEF electrophoresis, a sensitive technique for the determination of DNA double-strand breaks"; *International Journal of Radiation Biology*, vol. 56, No. 4, 437–448 (1989) no month available.

Cedervall; Abstract of "Joint Meeting of ARR, NRS, SRS"; Apr. 1–7, 1992, St. Andrews University.

Radford et al.; "I-induced DNA double strand breaks: use in calibration of the neutral filter elution technique and comparison with X-ray induced breaks"; *International Journal of Radiation Biology*, vol. 48, No. 4, 555–566 (1985) no month available.

Olayasu et al.; "Variation through the cell cycle in the dose–response of DNA neutral filter elution in X-irradiated synchronous CHO—cells"; *International Journal of Radiation Biology*, vol. 3, No. 5, 729–747 (1988) no month available.

Ager et al.; "Measurement of Radiation-Induced DNA Double-Strand Breaks by Pulsed Field Gel Electrophoresis"; *Radiation Research*, 122, 181–187 (1990) no month available.

Peak et al.; "Comparison of repair of DNA double-strand breaks caused by neutron or gamma radiation in cultured human cells"; *International Journal of Radiation Biology*, vol. 60, No. 6, 891–898 (1991) no month available.

Wlodek et al.; "Comparison between Pulsed-Field and Constant-Field Gel Electrophoresis for Measurement of DNA Double-Strand Breaks in Irradiated Chinese Hamster Ovary Cells"; *International Journal of Radiation Biology*, vol. 60, No. 5, 779–790 (1991) no month available.

Nathakarnkitkool et al.; "High-Resolution Capillary Electrophoretic Analysis of DNA in Free-Solution"; *Electrophoresis*, 13, 18–31 (1992) no month available.

Gu et al.; "Recovery of DNA from Agarose Gels Using a Modified Elutrap TM"; *Journal of Biochemical and Biophysical Methods*, 24, 45–50 (1992) no month available.

Ahn et al.; "Direct measurement by Pulsed-Field Gel Electrophoresis of Induction and Rejoining of X-ray Double Strand Breaks in Cultured Mouse Cells"; *International Journal of Radiation Biology*, vol. 59, No. 3, 661–675 (1991) no month available.

Hutchinson; "On the Measurement of DNA Double-Strand Breaks by Neutral Elution"; *Radiation Research*, 120, 182–186 (1989) no month available.

FREE SOLUTION ELECTROPHORESIS-MEMBRANE FILTERS TRAPPING ASSAY APPARATUS AND METHOD

TECHNICAL FIELD

This invention generally relates to an apparatus and method for classifying electrically charged particles according their size by electrophoresis using a free run solution and cascade membranes having different pore sizes. More particularly, the invention relates to an apparatus and method for classifying large macromolecules or their fragments by molecular size.

BACKGROUND OF THE INVENTION

There are different known apparatus and methods, e.g., ultrafiltration, chromatography, HPLC and the like, for classifying extremely small, charged particles. Unfortunately, problems exist especially with separation of living cells, native DNA, DNA having double strand breaks (dsb), RNA, viruses, proteins, polymer molecules, metal molecule aggregates and powders and the like. The problems associated with classifying DNA molecules and their fragments will be discussed, it being understood that problems exist in classifying other particles.

The measurement of radiation or drug-induced DNA damage is fundamental to many aspects of radiation and medical research because DNA is recognized as the most important target for radiation and some drug-induced cell killing. DNA dsb have been associated with cell killing and other deleterious effects of ionizing radiation. DNA fragments are the result of dsb.

It is desirable to not only study the level of dsb induced by a small, nonlethal dose of radiation or drugs to determine the dose's relevance to cell killing but also induced by a large superlethal dose. A superlethal dose exceeds the dose range studied in cell survival experiments and therefore the cell cannot survive such a dose.

The level of dsb is indicated by the reduction in the average size of the DNA molecules in the test cells as compared to the size of the DNA molecules of untreated control cells. The sizes of the DNA fragments can be measured by the fragments' rates of sedimentation using a sucrose gradient sedimentation assay that includes a centrifugation step, nondenatured (or neutral) filtration through a 0.2 micron filter using a filter elution assay, or by electrophoretic mobility using a Pulsed Field Gel Electrophoresis (PFGE) assay. These assays, based on widely different physical principles, can also be applied to measure the reduced mobility and increased size of DNA fragments due to formation of DNA-DNA or DNA-protein crosslinks.

The sensitivity of these assays (defined as the ability to detect dsb caused by small doses) is in part determined by how the DNA samples had been prepared. For example, sucrose gradient sedimentation assay involves pipeting isolated DNA which causes shear forces that fragment the DNA and gives an unreliable result. Consequently, superlethal doses have to be used to minimize the relative amount of dsb induced by sample preparation. Centrifugation can take up to 96 hours to complete, which is an undesirably long time. It cannot classify the fragments based on size. When cells are lysed in a non-ionic detergent and high salts (above 2M NaCl), the DNA is isolated free of structured proteins, such as histones, and it exists as a long fragile polymer which readily fragments during centrifugation which is undesirable. This assay requires expensive, sophisticated equipment that must be operated by a skilled worker.

PFGE uses electrical fields that periodically change direction instead of a constant field in one direction as occurs in conventional electrophoresis. The resolution of large molecules is primarily accomplished by exploiting the time that the molecule takes to change directions in response to the changing electrical fields. DNA migration is achieved by using a longer pulse time and/or a higher field in the forward direction. A number of different apparatuses have been described based primarily on variations in geometry of the electrical field. Depending on the DNA trapped, PFGE can take from 72 hours up to 10–15 days to perform, which is also an undesirably long time.

In filter elution, a sample is collected for a time period that starts when the first drop is eluted. After the collection time period ends, a second sample is collected. This is repeated for at least 17 hours which is an undesirably long time. The amount collected during each time period is compared to the other amounts collected. The contents of the samples are not analyzed. The smaller the collection time period, the more accurate the assay but the more difficult the sample collecting and the longer it takes to run the assay.

Other problems with these apparatus and methods have been noted, as discussed below.

Difficulties in measurement of dsb has contributed to the lack of definitive understanding of the role of the dsb in cell killing. Blazek et al., Evidence from non-denaturing filter elution that induction of double-strand breaks in the DNA of Chinese Hamster V79 cells by $\gamma$ radiation is proportional to the square of dose. *Radiation Research* 119, 466–477 (1989).

The main difficulty lies in detecting dsb in mammalian cells at low doses. Dsb have usually been determined by lysing cells in detergents on the top of neutral sucrose gradients and sedimenting the freed DNA through the gradient to estimate its relative molecular mass. This method has proved suitable for organisms with a small amount of chromosomal DNA such as bacteria or yeast. However, under similar conditions the large amount of DNA of a mammalian cell sediments in an anomalous fashion, even when the DNA is largely freed from membranes and other cellular components, unless large [superlethal] dosages of radiation are given (100 Gy$\leq$D$\leq$2000 Gy). Thus, molecular studies of dsb induction and repair have usually been carried out at dosages far in excess of those used for cell survival studies. Although other methods have been developed for the measurement of dsb at relatively low dosages, the calibration of these methods requires an absolute measurement of dsb within the same dose range. Blocher, DNA double-strand breaks in Ehrlich ascites tumor cells at low doses of X-rays. I. Determination of induced breaks by centrifugation at reduced speed. *Int J. Radiat, Biol.*, 42:3, 317–328 (1982).

See, Bradley, M. O. and Kohn, K. N., X-ray induced DNA dsb production and repair in mammalian cells as measured by neutral filter elution., *Nucleic Acid Research*, 7, 793–804 (1979) for additional shortcomings of filter elution.

PFGE is undesirable for use with large DNA molecules, e.g., mammalian DNA that containing $6 \times 10^9$ nucleotide pairs, that are 55 to 60 centimeters long and therefore have a high axial rotation. This is because it is difficult for the DNA to move through the gel without getting trapped therein. Viovy et al., Irreversible trapping of DNA during cross-field gel electrophoresis. *Electrophoresis*, 13, 1–6 (1992). For a review of PFGE, see, D. Cantor et al., Pulsed-field gel electrophoresis of very large DNA molecules. *Annual Review of Biophysical and Biophysical Chemistry*, 17, 287–304 (1988).

Because of the large molecular weight of mammalian DNA, anomalous sedimentation patterns are often observed on sucrose gradients and reliable molecular weights can be determined only at superlethal dosages of ionizing radiation. In the filter elution method, many extrinsic factors affect the rate at which the DNA elutes, e.g., pH of the lysis solutions, buffer composition, position of cells in the cell cycle and lysis conditions. Slow-speed centrifugation improves sensitivity, but is extremely dependent upon correct lysis. Stamato et al., Asymmetric field inversion gel electrophoresis: a new method for detecting DNA double-strand breaks in mammalian cells. *Radiation Research* 121, 196–205 (1990).

Conventional electrophoresis is limited to the separation of DNA molecules below 0.75 megabase pairs (Mbp) because larger DNA molecules orient along the direction of the electrical field and move irrespective of their molecular weight ("reptation"). The orientation also occurs during neutral gradient sedimentation (movement of DNA molecules under the force of a centrifugal field). The elongation of large molecules is not only determined by the laws of hydrodynamics, but is also an unavoidable necessity in agarose gel electrophoresis because the diameter of the gel pores is much smaller than that of the random coil of a DNA molecule, even at low concentrations. Thus, DNA molecules can only migrate through the agarose gel by being elongated and reptating through the chain of gel pores. Blocher et at., CHEF electrophoresis, a sensitive technique for the determination of DNA double-strand breaks *International Journal Of Radiation Biology* 56:4, 437–448 (1989). Reptation is a problem because it makes the test results inaccurate.

An addition problem with PFGE is DNA trapping in the gel matrix of the specimen or trapping in the gel fibers along the plate in so called "fight knots", which do not permit DNA molecules to move. Tarreel, C. et at., Irreversible Trapping of DNA during Crossed Field Gel Electrophoresis, *J. Nucleic Acids Research*, 18, 569–575 (1990) and Viovy, J-L. et at., *Electrophoresis*, 13, 1–6 (1992).

Typically, agarose gel is used in an amount in the range of about 0.75 to about 1 wt %. This concentration results in a gel that hinders the movement of high molecular weight particles therethrough.

About 20% and more of the DNA in a sample that is irradiated with high dosage ionizing radiation is not released from the gel of the sample despite having a large number of dsb. Thus, the accuracy of the assay is questionable.

Radioactive labeling of the DNA is usually required regardless of the apparatus or method used. Unfortunately, radioactive labeling limits the applicability to established cell lines and excludes primary tissues and non-proliferating cells.

Presently, food is being preserved by irradiation. Unfortunately, the above described DNA based assays cannot identify irradiated food.

Thus, it has been recognized that the most of the currently available techniques for measuring DNA dsb are time consuming and relatively expensive, have many shortcomings in reproducibility, sensitivity and applicability to most of the important particles to be studied (particularly chromosomal DNA from mammalian cells). Critical assessment of the available techniques leads to a general agreement that sensitivity of current assays for quantification of DNA dsb is a major problem. Also, all the assays suffer from an inability to produce purified DNA for analysis without inducing additional fragmentation.

An apparatus and method exhibiting the ability to classify particles by size and which do not exhibit the above-identified shortcomings and problems of the known apparatus and method are highly desirable.

SUMMARY OF THE INVENTION

The invention provides a Free Solution Electrophoresis Membrane Trapping Assay (FSEMTA) apparatus and method to classify extremely small, electrically charged particles by size, e.g., molecular weight, length or shape. The apparatus and method can be used with particles such as living cells, DNA, DNA having double stand breaks (dsb), RNA, proteins, polymers, metal molecule aggregates and powders, and the like. Many of these extremely small particles can be considered large macro-molecules, e.g., DNA, RNA, viruses, proteins and the like. The apparatus is relatively inexpensive. Classification can be completed in only about three to about five hours.

According to the invention, the apparatus includes a first porous membrane having a first pore size and a container. The container defines a cavity to receive the first membrane which seals the cavity to partially define a first chamber capable of holding a run solution. A specimen contains the particles to be classified and is held in a holder. The holder is received in the cavity with the first chamber being between the first membrane and the holder. A power supply is used to place a voltage (which creates a constant electric field) across the specimen, the run solution and the first membrane. A pump recirculates run solution within the chamber and can be used to cool the run solution to minimize the temperature increase caused by the voltage.

Preferably, the apparatus contains multiple membranes that define chambers therebetween within the container. The membranes are arranged in descending pore size with the membrane having the largest pore size being closest to the specimen. These chambers are capable of holding the run solution. The pump can recirculate the run solution contained in the chambers.

The power supply is set to apply an initial voltage across the specimen, run solution and membrane(s) and is then turned on. After a time period, the voltage is reduced. At the end of another time period, the voltage can again be reduced. By starting at the higher, initial voltage, it is presently theorized that the smaller particles are quickly freed from the specimen and enter the run solution. At the reduced voltages, larger particles are released into the run solution. In this way, the smaller particles can be separated from the larger particles prior to entry into the run solution using the voltage. Thus, the larger molecules do not effect the movement of the smaller particles.

Particles that are smaller in size than the pore size of the membrane pass therethrough and enter the run solution in the next chamber. Particles that are larger than the pore size of the membrane do not pass therethrough. Particles that pass through the membrane continue to move through the apparatus until they are retained by a membrane or they pass through the last membrane. Thus, the particles "cascade" through the apparatus. The particles on the membranes are then conventionally analyzed to determine the quantity of particles on each membrane using an appropriate, known detector. Thus, the particles are classified by size.

The particles can be removed from the membranes and used for different purposes, e.g., DNA cloning, flotation, separation of needed cells and the like.

The invention is also to a method of classifying particles by size. The particles are placed in a specimen that is juxtaposed with a run solution. The run solution is juxtaposed with a first porous membrane having a first pore size. Preferably, more than one porous membrane is used and they are arranged sequentially by pore size with the membrane having the largest pore size being closest to the specimen and that having the smallest pore size being farthest from the specimen. The chambers between the adjacent membranes are filled with run solution. An initial voltage applied across the specimen, run solution and membrane(s) causes particles to be released into the run solution and to move therethrough. The particle passes through membranes whose pore size is greater than the particle's size and enters the run solution in the next chamber. If the pore size is less than the particle's size, than the particle is retained. The voltage is reduced after a time period to facilitate the release of particles of a size that is greater than the previously released particles. The membranes are then removed and the number of particles on each membrane is conventionally determined.

The specimen is preferably prepared by embedding cells in a gel followed by lysis to remove the cell membrane and cytoplasm and to obtain purified DNA.

The apparatus and method can be used to detect if cells, mammalian or vegetative, have been exposed to radiation by detecting the quantity of dsb in the DNA structure which can be useful for the identification of irradiated food. The dsb can be determined without the cell being exposed to a superlethal dosage. This is particularly useful when a human has been exposed to radiation for radiation therapy, accidental radiation exposure and the like. The apparatus can also be used to detect DNA dsb caused by other cytotoxic environmental agents, e.g., pesticides, chemicals and the like.

The apparatus and the method can be used in cancer diagnostic and therapy to assist in deciding which kind of therapy, radiation, chemo or both, to be applied in a particular case. The patient's sensitivity to radiation and chemotherapy can be determined by comparing the sensitivity of normal cells with the sensitivity of transformed, cancerous cells.

The use of the constant electrical field (as opposed to a pulsed field) and free run solution (as opposed to a gel) facilitate movement of the electrically charged particles to dramatically accelerate their speed and separation on the respective membranes. This is accomplished without the need to apply additional forces such as those used with other methods for separation, e.g., ultrafiltration, HPLC or PFGE. The use of the relatively low voltage that is decreased over time and the free run solution overcome the risk of introducing fragmentation.

The agarose concentration in the specimen is usually at least about 0.35 wt % and is preferably less than 0.75 wt %. This relatively low concentration permits relatively easy release of the particles yet produces a relatively solid agarose gel matrix.

The combination of the voltage that is decreased over time and the use of a gel having a relatively low concentration of agarose results in about 88 to about 90% of the DNA fragments being released. This is a significant improvement which increases the accuracy of the test.

The preparation of the specimen in a relatively solid agarose gel matrix results in a high level of purification of DNA from its surroundings and associated proteins (such as histones) without inducing additional fragmentation. The DNA is in clear, empty cavities within the gel matrix. The cavities are the result of the removal of the non-DNA components of the cell and form a molecular sieve.

There is no need to use radioactive labeling of the DNA. Thus, the apparatus and method can be used with primary tissues and non-proliferating cells.

The apparatus and method do not result in DNA trapping thus overcoming this problem associated with PFGE.

Numerous other advantages and features of the present invention will become readily apparent from the following detailed description of the preferred embodiments and the appended claims.

DETAILED DESCRIPTION OF THE PREFERRED EMBODIMENTS

Although this invention is susceptible to embodiment in many different forms, there are described in detail herein, presently preferred embodiments of the invention. It should be understood, however, that the present disclosure is to be considered as an exemplification of the principles of this invention and is not intended to limit the invention to the embodiments described.

Figure 1:
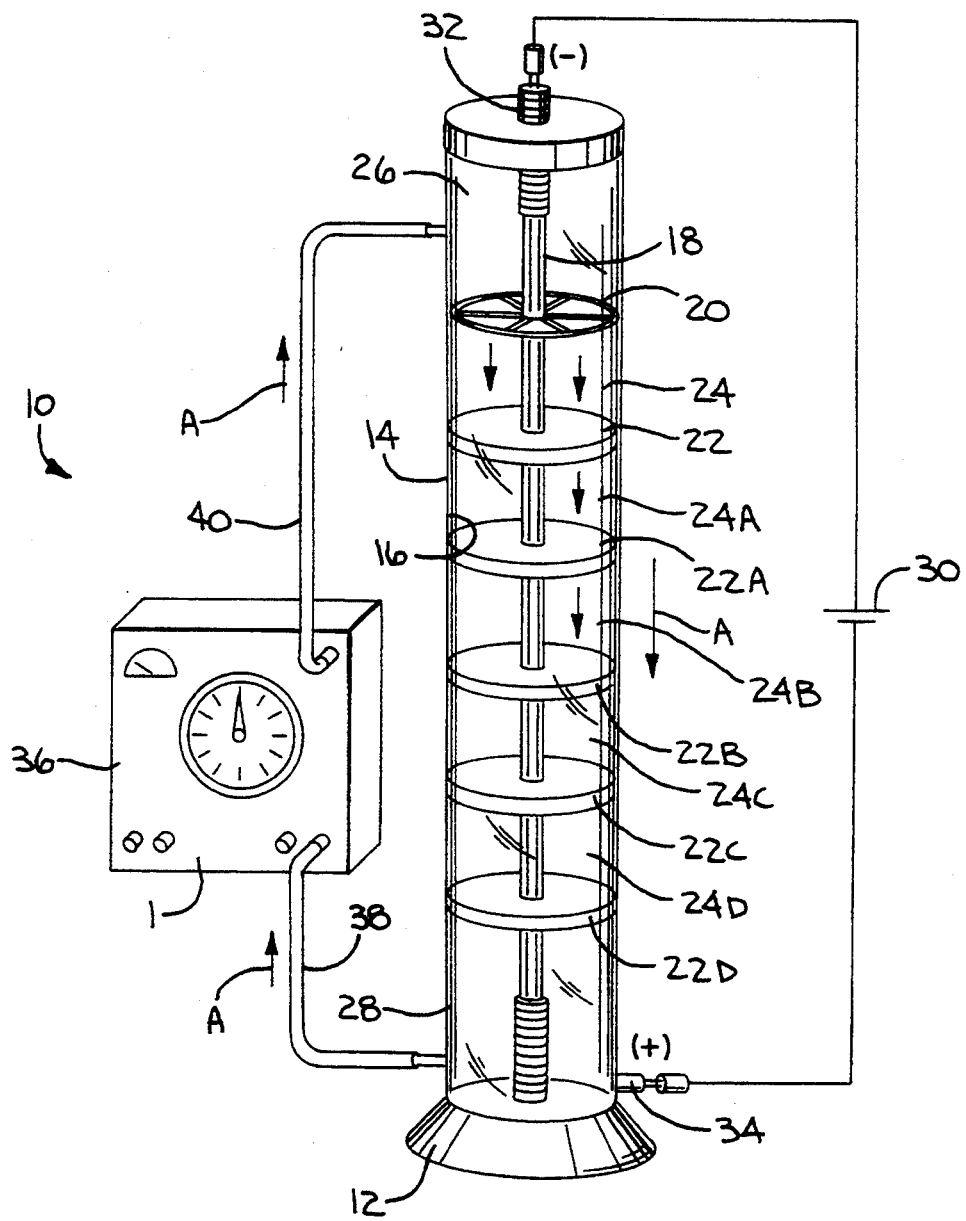
FIG. 1 illustrates a free solution electrophoresis-membrane trapping assay apparatus in accordance with the present invention.

FIG. 1, illustrates a free solution electrophoresis-membrane trapping assay apparatus 10 suitable for classifying small, electrically charged particles by size. The apparatus 10 has a base 12 that supports container 14 that is shown as an elongate container. A cavity 16 is defined by the container 14. Carrier 18 receives specimen holder 20 and first porous member 22 in a spaced relationship. The carrier 18 having holder 20 and first membrane 22 secured thereto is inserted into the cavity 16 and attached to the base 12. The first membrane 22 partially defines a first chamber 24 capable of holding a run solution (not shown). The first chamber 24 is defined by the holder 20, the first membrane 22 and the container 14. Upper space 26 and lower space 28 are defined by the container 14 and also the specimen holder 20 and the last membrane, respectively.

The term "free solution", as used in its various grammatical forms, indicates that the particles move through a solution that is free of gel, e.g., the particles move through a liquid run solution.

The apparatus 10 preferably has more than one membrane. The FIG. 1 illustrates a representative apparatus 10 having five membranes 22 to 22D that seal the cavity to partially define five chambers 24 to 24D. The apparatus 10 can have more or less than the five membranes illustrated. The membranes 22 to 22D are arranged in sequence by pore size with the membrane having the largest pore size being adjacent to the specimen holder 20 and the membrane having the smallest pore size being adjacent to the base 12.

A power supply (shown schematically) 30 can provide a variable, nonpulsed voltage, of direct current to produce an electric field across the container 14. The cathode 32 is shown adjacent to the specimen holder 20 and the anode 34 is shown adjacent to the last membrane. It being understood that the position of the cathode 32 and the anode 34 can be reversed depending on the charge of the particles being separated. The electrodes are preferably made from platinum wire when the apparatus is used to classify DNA.

Figure 2:
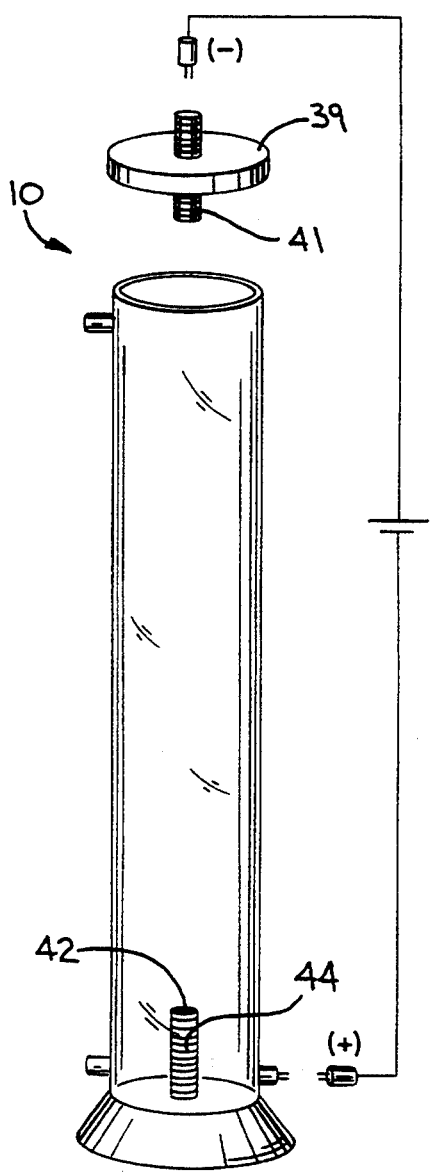
FIG. 2 illustrates an empty container and a pump of the present invention.

As shown in FIG. 2, the apparatus 10 includes cover 30 having tube 41 extending vertical therefrom and tube 42 extending vertical from the base 12. As can best be seen on the tube 42, a wire is wound about the tubes 41, 42 to make them the anode and cathode. The tubes 41, 42 are hollow and receive the carder 18 therein.

A recirculation pump 36 is in fluid communication with the lower space 28 through tubing 38 and in fluid communication with the upper space 26 through outlet tubing 40. Recirculation helps regulate the temperature of the run solution by passing the run solution through within the tubing through a cooling medium such as ice water to maintain a constant temperature.

Figure 3:
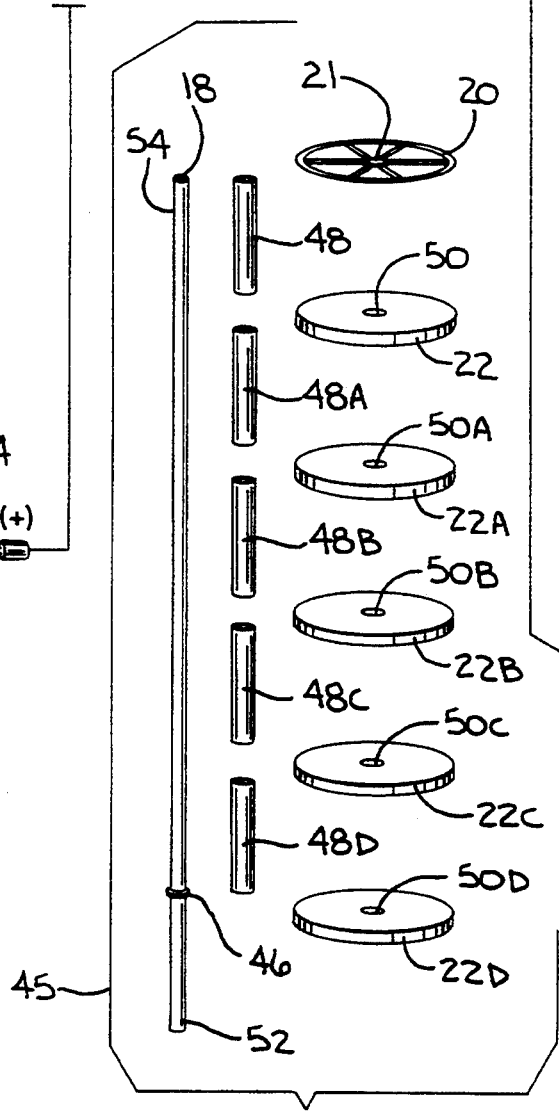
FIG. 3 illustrates the elements of a disassembled carder, holder and membranes of the present invention.
Figure 4:
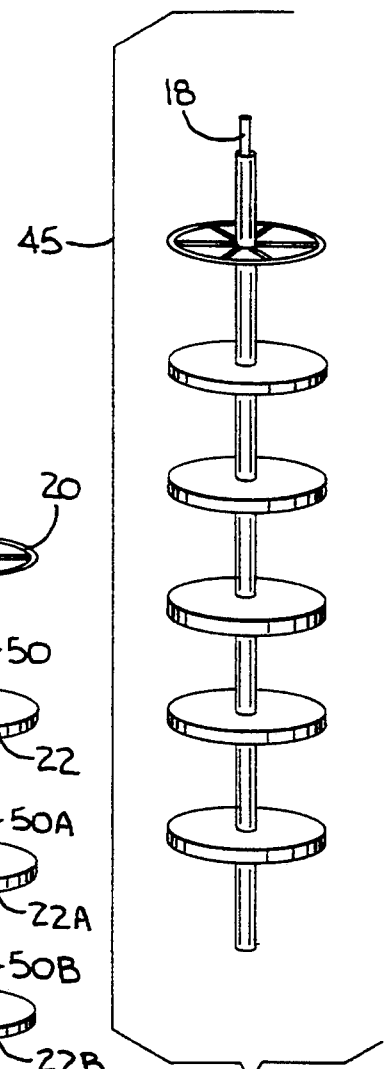
FIG. 4 illustrates an assembled carrier, holder and membranes of the present invention.

FIG. 3 illustrates a disassembled insert 45 of the apparatus 10. The insert 45 includes the carrier 18, the holder 20 having a hole 21 therethrough, the membranes 22 to 22D having holes 50 to 50D therethrough and spacers 48 to 48D. To assemble the insert 45, the carrier 18 is inserted through the hole 50D in the membrane 22D is placed in abutment with a retainer 46 on the carrier 18. Next, the carrier 18 is placed through the spacer 48D, the hole 50C in the membrane 22C etc. until the carrier 18 is placed through the spacer 48. Although the carrier 18 can be placed through the hole 21 of the holder 20 at this time, it is preferred that the assembled insert 45 first be inserted into the cavity 16 and the cavity 16 be filled with run solution prior to placing the carrier 18 through the holder 20 having the specimen thereon. The assembled insert 45 is shown in FIG. 4. The insert 45 is placed into the cavity 16 with the lower end 52 of the carrier 18 being received in the tube 42. After run solution and the specimen are in the cavity 16, the cover 30 is placed on the container 14 with the upper end 54 of the carrier 18 being received in the tube 41.

The method of classifying electrically charged particles contained in a specimen by size includes the steps of providing a first porous membrane having a first pore size that permits a portion of the particles to pass therethrough, positioning a run solution between the specimen and the membrane and applying an initial voltage across the specimen, run solution and membrane.

The terms "small" and "large", in their various gramatical forms, used herein to describe the particles being classified are relative terms to enable a description of what is presently theorized to be occurring. It being understood that all of the particles are extremely small.

An initial voltage is applied across the container 14 and hence also across the specimen, specimen holder 20, membranes 22 to 22D and the run solution (not shown) contained in the upper and lower spaces 26 and 28 and the chambers 24 to 24D. The pump 36 is turned on and moves the run solution in the direction indicated by the arrows "A" to recirculate the run solution within the container 14. The particles are attracted to, and move towards, the anode 34. (For positively charged particles, the cathode 32 would be placed at the base 12 to attract the particles through the membranes. This alternative is not illustrated.) By using an initial voltage that is relatively high, the smaller particles are rapidly released from the specimen and enter the run solution in the chamber 24. The smaller particles readily pass through the run solution and most, if not all, pass through the pores of the membrane 22. The smaller particles then enter the run solution in the chamber 24A and readily pass through the run solution. The sequence of particles passing through the pores, particles being retained by the membrane, particles that pass through the membrane entering the run solution and readily passing therethrough, are repeated until all the particles are retained by a membrane or pass through the last membrane. Thus, the particles "cascade" through the apparatus 10.

After a time period, and while the smaller particles are cascading through the apparatus 10, the voltage is reduced. The reduced voltage facilitates the release of larger particles from the specimen which enter the run solution in chamber 24. Some of the larger particles pass through the membrane 22 while others are retained thereby. The larger particles that pass enter, and readily pass through, the run solution in chamber 24A. This sequence continues for the larger particles as they cascade through the apparatus 10. The sequence of lowering the voltage to facilitate release of particles that are larger in size than the previously released particles, the released particles entering and readily passing through the run solution in the chamber, the membrane permitting passage or retaining the particles and the particles that pass through the membrane entering the run solution in the next chamber is repeated.

The voltage is turned off and the run solution drained from the apparatus 10. The membranes 22 to 22D are carefully removed. The classified particles in each membrane are then conventionally counted using appropriate method. Alternatively, the particles can be removed from the membranes and used for different purposes, e.g., DNA cloning, flotation, separation of needed cells and the like.

The apparatus and method are particularly well suited to classify extremely small electrically charged particles. Representative particles are DNA strands, DNA having double stand breaks (dsb), RNA, cells, viruses, proteins, polymer molecules, metal molecule aggregates and powders and the like. The extremely small particles can be considered large macromolecules, e.g., DNA, RNA, proteins and the like. The particles should move in response to being placed in the electric field created by the voltage. The apparatus and method are particularly useful in determining the amount of dsb resulting from exposure of the cell to radiation or some chemical agents (cytotoxins) used in oncology.

The specimen includes the particles and preferably also includes an optional binder material that holds the particles yet releases them in the presence of an electric field. A representative binder material is a gel.

Preparation of the particles varies, for example, polymer molecules and metal molecule aggregates or powder require only a minor amount of preparation. DNA, DNA having dsb and RNA that have been separated from the cellular membranes and cytoplasm, i.e., purified DNA, can also be embedded in the gel without additional preparation.

When the DNA is within the cell, the following protocol can be used to make the specimen having purified DNA. The protocol is especially useful in the preparation of DNA having very high molecular weight, e.g., DNA from eukaryotes (especially from mammalian cells), and for analyzing DNA having dsb. Furthermore, the protocol avoids the additional breakage to which high molecular weight DNA is extremely sensitive due to the high axial ratio.

The cells are subjected, as required, to homogenization, cell trypsinization and purification. Then, the cells are suspended in low temperature melting point agarose and about 0.5 to about 1 milliliters (ml) are layered in a 1.5 to about 2 millimeter (ram) thick specimen plug which is permitted to gel. The specimen plug is preferably shaped to have the same cross section as the cavity 16. After the gelling, it is necessary to destroy and discard the cellular membranes and cytoplasm by incubating the specimen with lysis solutions (that can contain cases enzymes) which vary in a known manner according to the type of cell being investigated. The incubation is performed in the presence of a concentration of ethylene dinitrilotetra-acetic acid (EDTA) effective to protect the DNA to be classified. Incubation is for a time period effective to destroy the cellular membranes and cytoplasm but not effect the DNA. Typically, the lysis is performed for a time period of about 30 minutes at a temperature of about 0° C. After lysis, the specimen is incubated a second time in another lysis buffer, e.g., ESP (10 Mm tris buffer [tris (hydroxymethyl) aminomethane], 0.5M EDTA, 1% N-Lauryl-sarcosine and 1 milligram/milliliter (mg/ml) proteinase K, pH 9-9.5), which is sometimes referred to as NDS. The second incubation lasts about two days at about 50° C. and is designed to destroy the nuclear membranes and the structural and binding proteins in the nuclei to produce stripped DNA.

Alternatively, the DNA can be purified by loading swollen cells on the top of 2.2M sucrose cushions that are then centrifuged to cause the relatively heavy cellular nuclei to pass through the cushion and the relatively light membrane debris and cytoplasm to remain on the cushion. Swollen cells are obtained by placing the cells in a known solution that penetrates the cell membrane to swell the cell. Swelling stretches the membrane which damages it making removal of the membrane easier. Then, the above protocol is performed but without the first lysis and washing steps.

The resultant stripped DNA contained in the plugs is then washed several times with PBS (0.14M NaCl, 0.01M NaH$_2$PO$_4$, pH 7.4). After treatment of cells to obtain stripped DNA, the DNA is in cavities in the gel that once contained the cells with the gel and cavities forming a molecular sieve.

To obtain a representative amount of DNA, the concentration of cells or nuclei per specimen is preferably in the range of about $10^5$ to about $10^7$.

A known problem of chromosomal DNA is its sensitivity to nucleases. This problem is resolved by using small, single use aliquots of all buffers and solutions with the buffers, solutions, materials and equipment that come in contact with the specimen being sterilized. The DNA should not contact metal objects because it can bond to the metal.

The membranes having know, definite pore sizes are arranged by pore size in descending order, i.e., with the membrane having the largest pore size being closest to the specimen. Although the pore size will depend upon the anticipated sizes of the particles, it has been found that arranging membranes having pore sizes of 8 μm, 5 μm, 3 μm, 1.2 μm, 0.8 μm, 0.45 μm and 0.2 μm is particularly well suited for classifying DNA macromolecules, especially DNA having dsb.

The membranes can be polycarbonate membranes commercially available from Nucleopore, Inc., Pleasanton, California, Millipore, N.H. or can be made of agarose gel with different concentrations instead of different pore size. The more agarose gel used, the smaller the pore size of the agarose gel membrane.

The run solution used in the container is preferably a run buffer, e.g., TBA (89 Mm tris, 89 Mm boric acid, 2.5 mM EDTA) or TAE (40 mM tris, 40 mM acetic acid, 2 mM EDTA). The concentration of the components of the run buffer can be varied to obtain the desired ionic strength.

The gelling agent, e.g., agarose, concentration in the specimen is usually at least about 0.35 weight percent (wt %) and preferably less than 0.75 wt %, based on the total weight of the specimen. This relatively low concentration permits easy release of the particles from the gel yet produces a relatively solid gel matrix within which the particles can be treated.

The voltage is preferably in the range of about 0.5 to about 10 volts per centimeter (V/cm). The voltage is decreased, preferably by less than 1 V/cm, at time intervals, preferably about 5 to about 15 minutes, to permit the smaller particles to be released into the run solution first and then allow larger and then larger particles to be released into the run solution. The voltage is preferable reduced the same amount and after the same time period to obtain a steady and consistent release of particles. Thus, the large particles can be recovered from the specimen without being trapped in the agarose gel of the plug and without interfering with the classification of the smaller particles. The use of the relatively low concentration of agarose gel and the varying voltage results in the specimen releasing about 88 to about 90% of the particles when the particles are DNA.

The electrophoresis is preferably carried out at a temperature of about 20° C.

The apparatus is calibrated with commercial DNA molecules having known length, usually bacterial and yeast DNA. The commercial DNA molecules can remain on respective membranes (as so called $R_r$ witnesses). The quantity of dsb in the DNA is determined using the previously prepared calibrations.

The pump 36 is preferably a peristaltic pump.

The following example is given by way of illustration, and not limitation.

EXAMPLE

Preparation of White Cell DNA From Whole Fresh Blood and Electrophoresis

Whole blood is collected in several 10 ml test tubes each containing 15 milligrams (mg) K$_3$EDTA. Approximately 13 ml of blood is transferred into 50 ml conical centrifuge flasks. The lysis buffer RBC (1 mM NH$_4$HCO$_3$, 114 mM NH$_4$Cl) is added to achieve a level of 50 ml. The flasks are gently mixed by rotation. The contents of the flasks are incubated at about 0° C. on ice for about 30 minutes to complete lysis. The flasks are then centrifuged for fifteen minutes at 3,000 revolutions per minute (rpm) at a temperature of 4° C. The supernatant is decanted. The precipitate is resuspended in 25 ml RBC lysis buffer and mixed gently by rotating. The contents of the flask is then incubated at about 0° C. on ice for about 5 to about 10 minutes to complete the lysis. The flasks are then centrifuged for about 15 minutes at about 3,000 rpm at a temperature of 4° C. The supernatant is decanted and the precipitate resuspended in 20 ml RBC lysis buffer with gentle mixing. The contents of the flask is then incubated at a temperature of about 0° C. on ice for a time period of about 5 minutes. The flasks are then centrifuged for 10 minutes at 3,000 rpm at 4° C. The supernatant is decanted off and the precipitate is resuspended in 20 ml of ice cold PBS. The contents of the flask is then centrifuged for 10 minutes at 2,500 rpm at 4° C. The supernatant is decanted and the precipitate containing the white cells is resuspended in 1.5 ml PBS. It is possible some residual red cells may be present.

Alternatively, the above procedure can be substituted with known procedures that use gradients such as Ficoll, Uromiro or Histopaque and the like.

To 0.5 to 1.5 ml of the resuspended precipitate is added 1.5 ml of a 1 wt % low melting temperature agarose aqueous solution followed by mixing. The mixture is carefully distributed onto a circular holder with 1 ml of the mixture being used to produce a 1.2 to 2 mm leveled layer. Solidification (gelling) of the agarose is achieved after about 15 minutes at room temperature or about 5 minutes in a freezer. The solidified white cell—containing agarose is opaque and is placed in a flask filled with EPS lysis buffer and maintained at 50° C. for a time period of two days with a gentle shaking. Lysis is indicated by the specimen becoming clear. The specimen is washed several times in run buffer. The specimen can be stored in EPS at a temperature of 4° C. for about two weeks in sterile conditions prior to use.

The apparatus is then prepared by cleaning and sterilizing all the components. The cavity is filled with TBA or TAE run buffer. The Nucleopore polycarbonate membranes are carefully assembled on the central carder, the specimen rand specimen holder are then assembled on the carder and the carrier is then inserted into the cavity. Additional buffer is added until it reaches the top of the container. The cover with the cathode then is placed on top. The peristaltic pump is switched on to keep the temperature at about 20° C. The voltage is turned on and set at 10 V/cm. The voltage is decreased at 10 minute intervals by 0.5 V/cm until the voltage reaches 0.5 V/cm. The movement of the DNA can be monitored by adding staining material, e.g., acridine orange, ethidium bromide, Hoechst 33258 and the like, to the run buffer. These stained DNA remaining on the membranes can be observed under a UV light.

Electrophoresis is completed in about 3 to about 5 hours. The power supply and peristaltic pump are shut off. The membranes are carefully demounted. The DNA is recovered from each membrane and from the agarose gel using appropriate, well known procedures and solutions. Conventional instruments are used to measure or indicate the presence of DNA after labeling or staining with the appropriate material. The calibration data and the results of the electrophoresis are compared to quantify the dsb in the DNA.

It is presently theorized that the above-described advantages are achieved because of the use of a low concentration of agarose gel in the specimen, a run solution (as opposed to a solid gel) and starting with a high initial voltage and reducing the voltage over time. The protocol for preparing the specimen is presently theorized to permit purification of the DNA without breaking the DNA.

The use of the cascade membranes with different pore size allows precise classification of the particles because the particles remain on the membrane having the appropriate pore size. This permits reproducibility of the method and classification with a high level of resolution.

The method permits direct estimation of the size of the classified particles. The estimation can be used to determine the molecular weight of the DNA fragments and to count the number of DNA dsb. The estimation of the DNA is obtained using calibration data on DNA with a known molecular size that is usually bacterial or yeast DNA.

This invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

What is claimed is:

1. A method of classifying, by size, electrically charged particles contained in a specimen, the method comprising the steps of:
   providing a first porous membrane having a first pore size that permits a portion of the particles to pass therethrough;
   positioning a run solution adjacent to the membrane;
   applying an initial voltage across the specimen, run solution and membrane; and
   reducing the initial voltage.

2. The method of claim 1 further comprising the step of recirculating the run solution.

3. A method of classifying molecules contained in a sample by size, the method comprising the steps of:
   (1) preparing a sample containing molecules wherein the molecules are obtained from cells having a nucleus, the preparation comprising the steps of:
      loading cells on a cushion;
      centrifuging the cushion and cells under conditions effective to permit the nuclei to pass through the cushion; and
   (2) providing a porous membrane;
   (3) positioning a run solution adjacent to the membrane; and
   (4) applying an initial voltage across the sample, run solution and membrane.

4. The method of claim 3 further comprising the step of recirculating the run solution.

5. A vertical, free solution electrophoresis, membrane filter trapping apparatus suitable for classifying of electrically charged particles by size, shape and weight, the particles, prior to classifying, being contained in a specimen, the apparatus comprising:
   a container having an elongate shape having upper and lower ends;
   a holder suitable to hold a specimen positioned on the upper end of said container, whereby the releasing of particles from a specimen is steady and causes preliminary separation of the particles by size, starting with releasing of smallest and finishing with largest particles;

a cascade of membrane filters, including first and last membrane filters, received in the container and having pore sizes, the membrane filters being arranged in sequence by pore size, with the first membrane filter having the largest pore size being adjacent the specimen holder on the upper end of the container to form a first chamber for free solution movement of particles between the specimen holder, the first membrane filter and the inner wall of the container, and last membrane filter having the smallest pore size and being adjacent to the lower end of the container and forming a last chamber with side walls of the lower end of the container;

electrodes, connectable to a suitable power supply of direct current, for creating an electrical field across said container; and means for assembling and disassembling of said specimen holder and said cascade membrane filters into and from said container, whereby membrane filters in said cascade can be very easily varied in numbers, depending on the number of different kinds of particles in the specimen to be classified and can be very easily disassembled for final recovery, investigation or other needs, the apparatus, the apparatus being capable of containing a free run liquid solution as a run buffer with predetermined strength, pH, temperature and constituents suitable to run electrophoretical movement of concrete particles, whereby particles can move freely in said solution with relatively high speed at very low viscosity.

6. The apparatus of claim 5 further comprising means for recirculating a free run liquid solution between said first chamber with said last chamber.

7. The apparatus of claim 6 wherein the recirculating means comprises a peristaltic pump.

8. The apparatus of claim 6 further comprising means for maintaining a free run liquid solution at a constant temperature.

9. The apparatus of claim 5 wherein the electrodes are vertically positioned, wound about tubes extended from the bottom and from the cover along an axis of the container, whereby a more homogeneous electrical field is created.

10. The apparatus of claim 5 further comprising means for assembling and disassembling the apparatus capable of being inserted into the container, the assembling and disassembling means comprise:

an elongate carder having a retainer in a lower part of the carder for retaining the last membrane filter;

a plurality of spacers with suitable dimensions, whereby determining the volume of the chambers and the length particles travel between membranes; and a pair of tubes having holes to receive said carrier positioned one extended from the bottom of the container and the other from the cover.

11. The apparatus of claim 5 wherein said membrane filters are built from synthetic polycarbonate material.

12. The apparatus of claim 5 further comprising means for recirculating the free run liquid solution.

13. A free solution electrophoresis membrane trapping assay method of classifying, by size and shape, electrically charged particles contained in a specimen, the method comprising the steps of:

providing a container having therein at least one porous membrane having a predetermined, well defined pore size;

providing a specimen holder;

providing a specimen containing electrically charged particles;

placing the specimen on the specimen holder;

positioning a free run solution in the container; and applying an initial high voltage across the specimen, run solution and at least one porous membrane, the voltage being in the range of about 0.5 to about 10 volts per centimeter, the initial high voltage being decreased a predetermined amount at predetermined time intervals to facilitate steady and consistent release of macromolecules by size.

14. A free solution electrophoresis membrane trapping assay method of classifying, by size and shape, electrically charged particles contained in a specimen, the method comprising the steps of:

providing a container having therein at least one porous membrane having a predetermined, well defined pore size;

providing a specimen holder;

providing a specimen containing electrically charged particles;

placing the specimen on the specimen holder;

positioning a free run solution in the container;

applying an initial appropriate voltage across the specimen, run solution and at least one porous membrane; and calibrating the classification of the particles using commercially available DNA having a known length.

15. A free solution electrophoresis membrane trapping assay method of classifying, by size and shape, electrically charged particles contained in a specimen, the method comprising the steps of:

providing a container having therein at least one porous membrane having a predetermined, well defined pore size;

providing a specimen holder;

providing a specimen containing DNA macromolecules obtained from whole cells or purified cellular nuclei;

embedding the cells or nuclei in age plug containing about 0.35 to about 0.75 wt % agarose gel;

placing the embedded specimen on the specimen holder;

positioning a free run solution in the container; and applying an initial voltage across the specimen, run solution and at least one porous membrane.

* * * * *